(12) United States Patent
Marks et al.

(10) Patent No.: US 7,947,837 B2
(45) Date of Patent: May 24, 2011

(54) ORGANIC SEMICONDUCTOR MATERIALS AND METHODS OF PREPARING AND USE THEREOF

(75) Inventors: Tobin J. Marks, Evanston, IL (US); Antonio Facchetti, Chicago, IL (US); He Yan, Skokie, IL (US)

(73) Assignee: Polyera Corporation, Skokie, IL (US)

( * ) Notice: Subject to any disclaimer, the term of this patent is extended or adjusted under 35 U.S.C. 154(b) by 816 days.

(21) Appl. No.: 11/977,418

(22) Filed: Oct. 24, 2007

(65) Prior Publication Data
US 2008/0167435 A1  Jul. 10, 2008

Related U.S. Application Data

(60) Provisional application No. 60/854,345, filed on Oct. 25, 2006.

(51) Int. Cl.
*C07D 471/02* (2006.01)
*H01L 27/088* (2006.01)

(52) U.S. Cl. .......................... 546/37; 313/504; 313/499
(58) Field of Classification Search ................... 546/37; 313/504, 499
See application file for complete search history.

(56) References Cited

U.S. PATENT DOCUMENTS

| | | | |
|---|---|---|---|
| 2,087,133 A | 7/1937 | Vollmann | |
| 4,378,302 A | 3/1983 | Aftergut et al. | |
| 4,611,385 A | 9/1986 | Forrest et al. | 29/574 |
| 4,846,892 A | 7/1989 | Henning et al. | |
| 5,405,962 A | 4/1995 | Muellen et al. | |
| 5,472,494 A | 12/1995 | Hetzenegger et al. | |
| 5,539,100 A | 7/1996 | Wasielewski et al. | |
| 5,677,417 A | 10/1997 | Muellen et al. | |
| 5,808,073 A | 9/1998 | Böhm et al. | |
| 5,908,583 A | 6/1999 | Havinga et al. | |
| 5,986,099 A | 11/1999 | Müllen et al. | |
| 6,051,351 A * | 4/2000 | Hsiao et al. | 430/59.1 |
| 6,060,601 A * | 5/2000 | Langhals et al. | 546/37 |
| 6,063,181 A | 5/2000 | Bohm et al. | |
| 6,084,099 A | 7/2000 | Hackmann et al. | |
| 6,099,636 A | 8/2000 | Henning et al. | |
| 6,124,458 A | 9/2000 | Müellen et al. | |
| 6,143,905 A | 11/2000 | Bohm et al. | |
| 6,165,661 A | 12/2000 | Hsiao et al. | |
| 6,184,378 B1 | 2/2001 | Bohm et al. | |
| 6,252,245 B1 | 6/2001 | Katz et al. | |
| 6,287,738 B1 | 9/2001 | Duff et al. | |
| 6,326,494 B1 | 12/2001 | Bohm et al. | |
| 6,348,595 B1 | 2/2002 | Hendi | |
| 6,403,796 B1 * | 6/2002 | Duff et al. | 546/37 |
| 6,486,319 B1 | 11/2002 | Böhm et al. | |
| 6,533,857 B1 | 3/2003 | Schmid et al. | |
| 6,551,717 B2 | 4/2003 | Katz et al. | 428/447 |
| 6,585,914 B2 | 7/2003 | Marks et al. | |
| 6,608,323 B2 | 8/2003 | Marks et al. | |
| 6,656,651 B1 | 12/2003 | Bender et al. | |
| 6,727,318 B1 | 4/2004 | Mathauer et al. | |
| 6,784,301 B2 | 8/2004 | Hackmann et al. | |
| 6,806,368 B2 | 10/2004 | Wurthner et al. | |
| 6,878,825 B2 | 4/2005 | Krieger et al. | |
| 6,890,377 B2 | 5/2005 | Böhm et al. | |
| 6,916,928 B2 | 7/2005 | Becker et al. | |
| 6,986,811 B2 | 1/2006 | Könemann et al. | |
| 7,083,675 B2 | 8/2006 | Mizuguchi et al. | |
| 7,105,046 B2 | 9/2006 | Mizuguchi et al. | |
| 7,105,674 B2 | 9/2006 | Hackmann et al. | |
| 7,326,956 B2 | 2/2008 | Shukla et al. | |
| 7,422,777 B2 | 9/2008 | Shukla et al. | |
| 2003/0181721 A1 | 9/2003 | Wurthner et al. | |
| 2003/0219625 A1 | 11/2003 | Wolk et al. | |
| 2004/0013959 A1 | 1/2004 | Bender et al. | |
| 2004/0023061 A1 | 2/2004 | Kathirgamanathan et al. | |
| 2005/0075453 A1 | 4/2005 | Mathauer et al. | |
| 2005/0092982 A1 | 5/2005 | Mullen et al. | |
| 2005/0106415 A1 | 5/2005 | Jarikov et al. | |
| 2005/0131220 A1 | 6/2005 | Dung et al. | |
| 2005/0171252 A1 | 8/2005 | Schambony et al. | |
| 2005/0176970 A1 | 8/2005 | Marks et al. | |
| 2005/0222416 A1 | 10/2005 | Bohm et al. | |
| 2005/0238974 A1 | 10/2005 | Sekiya et al. | |
| 2005/0251930 A1 | 11/2005 | Erk et al. | |
| 2006/0058330 A1 | 3/2006 | Krieger et al. | |
| 2006/0075585 A1 | 4/2006 | Krieger et al. | |
| 2006/0131564 A1 | 6/2006 | Shukla et al. | |
| 2006/0134823 A1 | 6/2006 | Shukla et al. | |
| 2006/0141287 A1 | 6/2006 | Klubek et al. | |
| 2006/0210898 A1 | 9/2006 | Jubran | |
| 2006/0229385 A1 | 10/2006 | Boehm | |
| 2006/0237712 A1 | 10/2006 | Shukla et al. | |
| 2007/0026332 A1 | 2/2007 | Ferrar et al. | |
| 2007/0096084 A1 | 5/2007 | Shukla et al. | |
| 2007/0116895 A1 | 5/2007 | Shukla et al. | |
| 2008/0021220 A1 | 1/2008 | Marks et al. | |
| 2008/0135833 A1 | 6/2008 | Shukla et al. | |
| 2008/0161569 A1 | 7/2008 | Dung et al. | |
| 2008/0177073 A1 | 7/2008 | Facchetti et al. | |
| 2008/0185555 A1 | 8/2008 | Facchetti et al. | |
| 2008/0185577 A1 | 8/2008 | Facchetti et al. | |
| 2008/0249309 A1 | 10/2008 | Facchetti et al. | |

FOREIGN PATENT DOCUMENTS

DE  2951349 A1  7/1981

(Continued)

OTHER PUBLICATIONS

Baier et al., "Intermolecular energy transfer after vibrational excitation of a perylene dye in solution, in polymer binder, and in a side-chain copolymer," *J. Chem. Phys.*, 114: 6739-6743 (2001).

(Continued)

*Primary Examiner* — Charanjit S Aulakh
(74) *Attorney, Agent, or Firm* — K&L Gates LLP

(57) ABSTRACT

Solution-processable organic n-type semiconductor materials are provided with processes for preparing the same. Composites and electronic devices including the organic n-type semiconductor materials also are provided.

11 Claims, 2 Drawing Sheets

FOREIGN PATENT DOCUMENTS

| | | |
|---|---|---|
| DE | 3434059 A1 | 3/1985 |
| DE | 3620332 A1 | 12/1987 |
| DE | 3703131 | 8/1988 |
| DE | 4018830 | 12/1991 |
| DE | 4338784 | 5/1995 |
| DE | 4440242 | 5/1996 |
| DE | 19501737 A1 | 7/1996 |
| DE | 19547210 A1 | 6/1997 |
| DE | 19622673 A1 | 12/1997 |
| DE | 19651712 A1 | 6/1998 |
| DE | 19709008 A1 | 9/1998 |
| DE | 10038672 A1 | 5/2002 |
| DE | 10148172 A1 | 4/2003 |
| EP | 0031065 | 10/1983 |
| EP | 0 217 256 | 4/1987 |
| EP | 0 422 535 | 4/1991 |
| EP | 0 826 740 | 3/1998 |
| EP | 0 861 878 | 9/1998 |
| EP | 0 896 964 | 2/1999 |
| EP | 0 990 951 | 4/2000 |
| EP | 1 172 700 | 1/2002 |
| EP | 1 671 674 | 6/2006 |
| FR | 1 526 496 | 5/1968 |
| FR | 2237922 | 2/1975 |
| JP | 05-025174 | 2/1993 |
| JP | 05-027459 | 2/1993 |
| JP | 11-119455 | 4/1999 |
| JP | 2002-302674 | 10/2002 |
| JP | 2003-327587 | 11/2003 |
| JP | 2004-093801 | 3/2004 |
| JP | 2004-093802 | 3/2004 |
| JP | 2004-152815 | 5/2004 |
| JP | 2005-154409 | 6/2005 |
| JP | 2005-189765 | 7/2005 |
| JP | 2005-209887 | 8/2005 |
| JP | 2006-028027 | 2/2006 |
| WO | 90/01480 | 2/1990 |
| WO | 96/22332 | 7/1996 |
| WO | 97/22607 | 6/1997 |
| WO | 97/22608 | 6/1997 |
| WO | 97/26301 | 7/1997 |
| WO | 98/32799 | 7/1998 |
| WO | 98/32802 | 7/1998 |
| WO | 98/49164 | 11/1998 |
| WO | 00/69829 | 11/2000 |
| WO | 02/14414 | 2/2002 |
| WO | 03/091345 | 11/2003 |
| WO | 03/104232 | 12/2003 |
| WO | 2004/029028 | 4/2004 |
| WO | 2005/047265 | 5/2005 |
| WO | 2005/070894 | 8/2005 |
| WO | 2005/070895 | 8/2005 |
| WO | 2005/078023 | 8/2005 |
| WO | 2005/092901 | 10/2005 |
| WO | 2005/124453 | 12/2005 |
| WO | 2006/021307 | 3/2006 |
| WO | 2006/037539 | 4/2006 |
| WO | 2006/050860 | 5/2006 |
| WO | 2006/093965 | 9/2006 |
| WO | 2006/115714 | 11/2006 |
| WO | 2007/074137 | 7/2007 |
| WO | 2007/093643 | 8/2007 |
| WO | 2008/091670 | 7/2008 |

OTHER PUBLICATIONS

Buncel et al., "Synthesis and characterization of [3,3]- and [3,4]-perinophane," *Tetrahedron Letters*, 42: 3559-3562 (2001).

Giaimo et al., "Excited-State Symmetry Breaking in Cofacial and Linear Dimers of a Green Perylenediimide Chlorophyll Analogue Leading to Ultrafast Charge Separation," *J. Am. Chem. Soc.*, 124: 8530-8531 (2002).

Holman et al., "Studying and Switching Electron Transfer: From the Ensemble to the Single Molecule," *J. Am. Chem. Soc.*, 126: 16126-16133 (2004).

Kwan et al., "Electrochemistry of Langmuir-Blodgett and Self-Assembled Films Built from Oligoimides," *Langmuir*, 8:3003-3007 (1992).

Langhals et al., "Tangentially Coupled π Systems and their Through-Space Interaction—Trichromophoric Perylene Dyes," *J. Prakt. Chem.*, 338: 654-659 (1996).

Langhals et al., "Chiral Bifluorophoric Perylene Dyes with Unusually High CD Effects—A Simple Model for the Photosynthesis Reaction Center," *Leibigs Ann./Recueil.*, 1151-1153 (1997).

Lindner et al., "Nanostructures of N-type organic semiconductor in a p-type matrix via self-assembly of block copolymers," *Macromolecules*, 37:8832-8835 (2004).

Lukas et al., "Femtosecond Optical Switching of Electron Transport Direction in Branched Donor-Acceptor Arrays," *J. Phys. Chem. B*, 104: 931-940 (2000).

Lukas et al., "Biomimetic Electron Transfer Using Low Energy Excited States: A Green Perylene-Based Analogue of Chloroophyll a," *J. Phys. Chem. B*, 106: 1299-1306 (2002).

Rodriguez-Llorente et al., "Infrared and Raman spectra of thin solid films of 1,2-bis(propylimido perylene) ethane," *Spectrochimica Acta. Part A*, 55: 969-978 (1999).

Rodriguez-Llorente et al., "Vibrational spectra and thin solid films of a bi(propylperylenediimide)," J. Mater. Chem., 8(10): 2175-2179 (1998).

Rodriguez-Llorente et al., "Spectroscopic characterization of thin solid films of a bis(chlorobenzylimidoperyleneimido)octane derivative," *J. Mater. Chem.*, 8(3): 629-632 (1998).

Tauber et al., "Electron Hopping in π-Stacked Covalent and Self-Assembled Perylene Diimides Observed by ENDOR Spectroscopy," *JACS Comm.*, 128: 1782-1783 (2006).

Ahrens et al., "Cyanated Perylene-3,4-dicarboximides and Perylene-3,4:9,10-bis(dicarboximide):Facile Chromophoric Oxidants for Organic Photonics and Electronics," *Chem. Mater.*, 15:2684-2686 (2003).

Chen et al., "Oligothiophene-Functionalized Perylene Bisimide System: Synthesis, Characterization, and Electrochemical Polymerization Properties," *Chem. Mater.*, 17:2208-2215 (2005).

Database Caplus [Online] Chemical Abstracts Service, Columbus, Ohio, US; May 12, 1984, XP002493285 retrieved from STN Database accession No. 1984:34294 abstract.

Database WPI Thomson Scientific, London, GB; AN 1983-750663 XP002493286 and JP 58 124790 A (Matsushita Electric Ind. Co. Ltd.) Jul. 25, 1983 abstract.

Facchetti et al., "Building Blocks for n-Type Organic Electronics. Regiochemically Modulated Inversion of Majority Carrier Sign in Perfluoroarene-Modified Polythiophene Conductors," *Angew. Chem. Int. Ed.*, 2003: 42, 3900-3903.

Facchetti et al., "n-Type Building Blocks for Organic Electronics: a Homologous Family of Fluorocarbon-substituted Thiophene Oligomers with High Carrier Mobility," *Adv. Mater.*, 2003: 15, 33-38.

Facchetti et al., "Tuning the Semiconducting Properties of Sexithiophene by a,w-Substitution—α, ω-Diperfluorohexylsexithiophene: the First n-Type Sexithiophene for Thin-film Transistors," *Angew. Chem. Int. Ed.*, 2000: 39, 4547-4551.

Huttner et al., "N-type organic field effect transistors from perylene bisimide block copolymers and homopolymers," *Appl. Phys. Lett.*, 92: 093302 (2008).

Jones et al., "Cyanonaphthalene Diimide Semiconductors for Air-Stable, Flexible, and Optically Transparent n-Channel Field-Effect Transistors," *American Chemical Society*, 2007: 19 (11), 2703-2705.

Jones et al., "High-Mobility Air-Stable n-Type Semiconductors with Processing Versatility: Dicyanoperylene-3,4:9, 10-bis(dicarboximides)," *Angew. Chem. Int. Ed.*, 43. 6363-6366 (2004).

Jones et al., "Tuning Orbital Energetics in Arylene Diimide Semiconductors. Materials Design for Ambient Stability of n-Type Charge Transport," *J. Am. Chem. Soc.*, 2007: 129, 15259-15278.

Lindner et al., "Charge Separation at Self-Assembled Nanostructured Bulk Interface in Block Copolymers," *Angew. Chem. Int. Ed.*, 45:3364-3368 (2006).

Martyushina et al., "Searches for Nondepolarizing Short-Action Myorelaxants," *Pharm. Chem.*, 1982: 16 (7), 801-806 (English translation).

Morris et al., "Synthesis of Extended Linear Aromatics Using Tandem Diels-Alder Aromatization Reactions," *J. Org. Chem.*, 59:6484-6486 (1994).

Müller et al., "Facile synthetic approach to novel core-extended perylene carboximide dyes," *Chem. Commun.*, (2005) 4045-4046.

Petit et al., "Synthesis of macromolecular substances comprising dye derivatives as monomeric units. III. Synthesis and study of monomeric dihydroxy dyes," *Bulletin de la Societe Chimique de France*, 7-8:1591-1596 (1974).

Rohr et al., "Liquid crystalline coronene derivatives," *J. Mater. Chem.*, 11:1789-1799 (2001).

Shimizu et al., "Convergent Functional Groups. 15. Synthetic and Structural Studies of Large and Rigid Molecular Clefts," *J. Am. Chem. Soc.*, 116:5145-5149 (1994).

Singh et al., "Soluble derivatives of perylene and naphthalene diimide for n-channel organic field-effect transistors," *Organic Electronics*, 7:480-489 (2006).

Thalacker et al., "Hydrogen bond directed self-assembly of core-substituted naphthalene bisimides with melamines in solution and at the graphite interface," *Org. Biomol. Chem.*, 3:414-422 (2005).

Tsoi et al., "Distributed Bilayer Photovoltaics Based on Nematic Liquid Crystal Polymer Networks," *Chem Mater.*, 19:5475-5484 (2007).

* cited by examiner

ORGANIC SEMICONDUCTOR MATERIALS AND METHODS OF PREPARING AND USE THEREOF

CROSS REFERENCE TO RELATED APPLICATION

This application claims priority to and the benefit of U.S. Provisional Patent Application Ser. No. 60/854,345, filed on Oct. 25, 2006, the disclosure of which is incorporated by reference in its entirety.

INTRODUCTION

Electronic devices based on "plastic" components such as organic thin film transistors (TFT), organic light emitting diodes (OLEDs), printable circuits, organic photovoltaic devices, capacitors and sensors have received much attention in the past few years. Similar to inorganic material-based electronics, organic-based devices can operate efficiently and at high speed if both p-type (where the charge carriers are substantially holes) and n-type (where the charge carriers are substantially electrons) semiconductor materials exhibit high carrier mobility and stability over time under ambient conditions, and can be processed in a cost-effective manner.

Currently, the most promising organic semiconductors include highly π-conjugated small molecules and polymers that have an electronic structure suitable for charge injection from the electrical contacts of a device as well as intermolecular ordering that allows efficient transport of gate-induced charge carriers. To date, the great majority of the electronic organic materials that have been investigated and optimized are based on p-type semiconductors due to their enhanced environmental stability. In contrast, the selection of n-type organic materials is limited to a very small number of molecules and polymers, most of them being inactive at ambient conditions.

Particularly promising classes of n-type semiconductor materials are perylene and naphthalene diimides (PDIs and NDIs, respectively). Along with fullerenes, unsubstituted perylene dianhydrides and PDIs, bearing only hydrogen atoms in the bay position (1-, 6-, 7-, and 12-positions), are considered to be the archetype of n-type semiconductor materials. Their application in solar cell devices, xerographic photoreceptors, and OFETs has been demonstrated. See e.g. Tang, C. W. (1986), *Appl. Phys. Lett.*, 48: 183; Law, K. Y. (1993), *Chem. Rev.*, 93: 449; and Forrest, R. F. (1997), *Chem. Rev.*, 97:1793.

Of the very few promising n-type semiconductors, most of them suffer from serious drawbacks including poor stability in air and poor solubility in common organic solvents, which limit potential manufacturing processes (e.g., various solution-based processes) and accordingly, make them difficult and/or expensive to synthesize. For example, while both contact and noncontact printing techniques have been employed to deposit and pattern materials for the fabrication of electronic devices, wider application of organic semiconductor materials in printable circuits has been hamstrung by the unavailability of suitable "ink" formulations. Even with relatively air-stable and soluble n-type organic semiconductor materials, satisfactory printing results can only be achieved if these n-type organic semiconductor materials can be formulated in much greater solution viscosity ranges than presently available. This problem is exacerbated by the fact that inclusion of binders is not a feasible option given their negative impact on carrier mobility.

Accordingly, there is a desire in the art for new n-type organic semiconductor materials that can be formulated in a broad range of solution viscosities for use with various solution processing techniques including, but not limited to, contact and noncontact printing.

SUMMARY

In light of the foregoing, the present teachings provide organic semiconductor materials and associated devices that can address various deficiencies and shortcomings of the prior art, including those outlined above.

More specifically, the present teachings provide organic semiconductor materials that are based upon compounds that include fused ring tetracarboxylic imide moieties. It has been found that dimeric and polymeric compounds based upon fused ring tetracarboxylic imides can afford useful electrical properties while offering broad viscosity ranges suitable for various solution-phase processes.

In one aspect, the present teachings provide a dimeric compound having the formula:

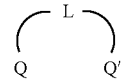

wherein Q and Q' are independently a fused ring tetracarboxylic imide and L is a linker connecting the two Q and Q' groups. L can be a symmetrical or unsymmetrical linker as described below.

In another aspect, the present teachings provide a polymeric compound having at least one repeating unit that includes a pendant group of the formula L-Q, where for each repeating unit including a pendant group L-Q, each Q independently is a fused ring tetracarboxylic imide, and each L independently is a linker or a covalent bond.

In a further aspect, the present teachings provide a copolymeric compound having at least one repeating unit that includes a pendant group of the formula L-Q, where for each repeating unit including a pendant group L-Q, each Q independently is a fused ring tetracarboxylic imide, and each L independently is a linker or a covalent bond. The copolymeric compound can have at least one other repeating unit that does not include the pendant group L-Q.

The present teachings also provide various compositions, articles, structures, and devices that include the dimeric compounds, the polymeric compounds, and the copolymeric compounds disclosed herein.

The foregoing, and other features and advantages of the present teachings, will be more fully understood from the following figures, description, and claims.

BRIEF DESCRIPTION OF THE DRAWINGS

It should be understood that the drawings described below are for illustration purposes only and are not intended to limit the scope of the present teachings in any way.

DETAILED DESCRIPTION

Figure 1:
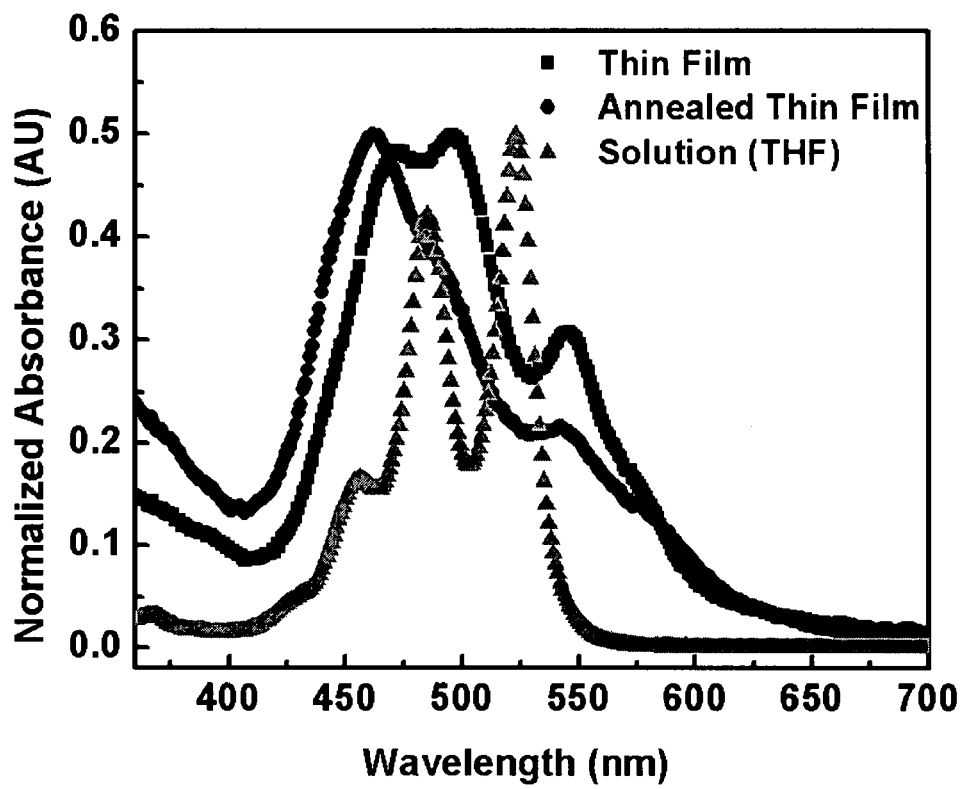
FIG. 1 provides UV-vis absorption spectra of solutions and thin films comprising compounds of the present teachings.

The present teachings relate to organic semiconducting compounds, methods for preparing the same, as well as to compositions, articles, structures, and devices that include such compounds.

The present teachings provide solution-processable, e.g., spin-coatable and printable, organic semiconductor materials (e.g., compounds and compositions) that exhibit useful electrical properties that can be used to fabricate various organic electronic articles, structures and devices. The organic semiconductor materials disclosed herein can be considered n-type semiconductor materials and can be used, among other applications, to build complementary circuits or circuitry that includes an n-type semiconductor material of the present teachings and a p-type semiconductor that is either inorganic or organic.

Specifically, the present teachings provide dimeric and polymeric compounds that are based upon fused ring tetracarboxylic imides. These dimeric and polymeric compounds typically have at least some solubility in one or more common solvents and can be stable in ambient conditions. The present teachings also provide compositions, articles, structures, and devices that include these compounds.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

The use of the terms "include," "includes," "including," "have," "has," or "having" should be generally understood as open-ended and non-limiting unless specifically stated otherwise.

It should be understood that the order of steps or order for performing certain actions is immaterial so long as the present teachings remain operable. Moreover, two or more steps or actions may be conducted simultaneously.

As used herein, "dimer" or "dimeric compound" refers to a molecule composed of two identical or similar moities covalently linked together. In some embodiments of the present teachings, the two identical or similar moities are represented by Q (and Q'), and a linker L is used to covalently link the two moities together.

As used herein, "polymer" or "polymeric compound" refers to a molecule consisting of at least three repeating units (monomers) connected by covalent chemical bonds. The polymer or polymeric compound can have only one type of repeating unit as well as two or more types of repeating units. In the latter case, the term "copolymer" or "copolymeric compound" can be used herein instead, especially when the polymer includes chemically significantly different repeating units. A polymer typically comprises a backbone with optional pendant groups. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. In some embodiments, a formula similar to the one below can be used to represent a copolymer, and such formula should be interpreted to embrace a copolymer having any repeating pattern consisting of x % of $Q^1$, y % of $Q^2$, and z % of $Q^3$, where $Q^1$, $Q^2$, and $Q^3$ are different repeating units:

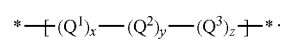

As used herein, "fused ring" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and can include, without limitation, rylenes having the formula:

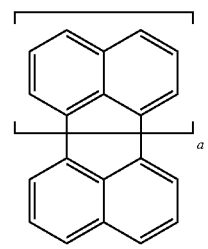

where a can be an integer in the range of 1-3; acenes, which are linear fused benzene rings and can be represented by the formula:

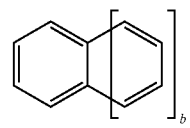

where b can be an integer in the range of 1-7, examples of which include, but are not limited to, naphthalenes, anthracenes, tetracenes, pentacenes, and hexacenes; and coronenes, which have the formula:

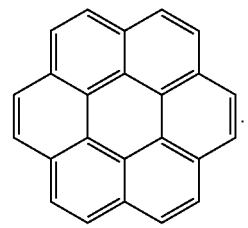

As used herein, "tetracarboxylic imide" refers to a compound having a

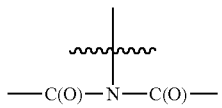

group and a —C(O)—Z—C(O)— group, where Z can be O, S, S(O), NR$^b$, C(O) or CR$^c$R$^d$; and R$^b$, R$^c$, and R$^d$ are as defined herein. The

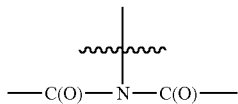

group and the —C(O)—Z—C(O)— group typically are not adjacent to each other.

As used herein, "fused ring tetracarboxylic imide" refers to a molecule comprising a polycyclic ring system having at least two rings where at least one of the rings is aromatic and such aromatic ring (carbocyclic or heterocyclic) has a bond in common with at least one other ring that can be aromatic or non-aromatic and that can be carbocyclic or heterocyclic, and a

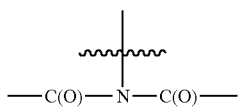

group and a —C(O)—Z—C(O)— group, where Z can be O, S, S(O), NR$^b$, C(O) or CR$^c$R$^d$; and R$^b$, R$^c$, and R$^d$ are as defined herein. The

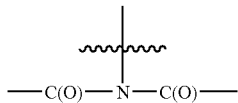

group and the —C(O)—Z—C(O)— group generally are not adjacent to each other, and typically are present on two different rings.

As used herein, "halo" or "halogen" refers to fluoro, chloro, bromo, and iodo.

As used herein, "amino" refers to —NH$_2$, an —NH-alkyl group, an —N(alkyl)$_2$ group, an —NH-arylalkyl group, an —N(alkyl)arylalkyl group, and an —N(arylalkyl)$_2$ group, and is within the definition of —NR$^1$R$^2$, wherein R$^1$ and R$^2$ are as defined herein.

As used herein, "alkoxy" refers to —O-alkyl group, and is within the definition of —OR$^3$, wherein R$^3$ is as defined herein. Examples of alkoxy groups include, but are not limited to, methoxy, ethoxy, propoxy (e.g., n-propoxy and isopropoxy), t-butoxy groups, and the like.

As used herein, "alkylthio" refers to an —S-alkyl group. Examples of alkylthio groups include, but are not limited to, methylthio, ethylthio, propylthio (e.g., n-propylthio and isopropylthio), t-butylthio groups, and the like.

As used herein, "ester" refers to both an —O—C(O)-alkyl group and a —C(O)—O-alkyl group, where the former group is within the definition of —OC(O)R$^3$, and R$^3$ is as defined herein.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and isopropyl), butyl (e.g., n-butyl, isobutyl, s-butyl, t-butyl), pentyl groups (e.g., n-pentyl, isopentyl, neopentyl), and the like. In various embodiments, an alkyl group can have 1 to 20 carbon atoms, i.e., a C$_{1-20}$ alkyl group. In some embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, s-butyl, t-butyl).

As used herein, "haloalkyl" refers to an alkyl group having one or more halogen substituents. Examples of haloalkyl groups include, but are not limited to, CF$_3$, C$_2$F$_5$, CHF$_2$, CH$_2$F, CCl$_3$, CHCl$_2$, CH$_2$Cl, C$_2$Cl$_5$, and the like. Perhaloalkyl groups, i.e., alkyl groups wherein all of the hydrogen atoms are replaced with halogen atoms (e.g., CF$_3$ and C$_2$F$_5$), are included within the definition of "haloalkyl." For example, a C$_{1-20}$ haloalkyl group can have the formula —C$_n$X$_{2n}$— or —C$_n$H$_{2n-t}$X$_t$—, wherein X is F, Cl, Br, or I, n is an integer in the range of 1 to 20, and t is an integer in the range of 0 to 40, provided that t is less than or equal to 2n.

As used herein, "alkenyl" refers to a straight-chain or branched alkyl group having one or more carbon-carbon double bonds. Examples of alkenyl groups include, but are not limited to, ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 20 carbon atoms, i.e., a C$_{2-20}$ alkenyl group.

As used herein, "alkynyl" refers to a straight-chain or branched alkyl group having one or more triple carbon-carbon bonds. Examples of alkynyl groups include, but are not limited to, ethynyl, propynyl, butynyl, pentynyl, and the like. The one or more triple carbon-carbon bonds can be internal (such as in 2-butyne) or terminal (such as in 1-butyne). In various embodiments, an alkynyl group can have 2 to 20 carbon atoms, i.e., a C$_{2-20}$ alkynyl group.

As used herein, "cycloalkyl" refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Examples of cycloalkyl groups include, but are not limited to, cyclopropyl, cyclopropylmethyl, cyclobutyl, cyclopentyl, cyclohexyl, cyclohexylmethyl, cyclohexylethyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like.

As used herein, "heteroatom" refers to an atom of any element other than carbon or hydrogen and includes, for example, nitrogen, oxygen, sulfur, phosphorus, and selenium.

As used herein, "cycloheteroalkyl" refers to a non-aromatic cycloalkyl group that contains at least one ring heteroatom selected from O, N and S, and optionally contains one or more double or triple bonds. One or more N or S atoms in a cycloheteroalkyl ring may be oxidized (e.g., morpholine N-oxide, thiomorpholine S-oxide, thiomorpholine S,S-dioxide). In some embodiments, nitrogen atoms of cycloheteroalkyl groups can bear a substituent, for example, a hydrogen atom, an alkyl group, or other substituents as described herein. Cycloheteroalkyl groups can also contain one or more oxo groups, such as piperidone, oxazolidinone, pyrimidine-2,4(1H,3H)-dione, pyridin-2(1H)-one, and the like. Examples of cycloheteroalkyl groups include, among others, morpholine, thiomorpholine, pyran, imidazolidine, imidazoline, oxazolidine, pyrazolidine, pyrazoline, pyrrolidine, pyrroline, tetrahydrofuran, tetrahydrothiophene, piperidine, piperazine, and the like.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have from 6 to 14 carbon atoms in its ring system, which can include multiple fused rings. In some embodiments, a polycyclic aryl group can have from 7 to 14 carbon atoms. Any suitable ring position of the aryl group can be covalently linked to the defined chemical structure. Examples of aryl groups having only aromatic carbocyclic ring(s) include, but are not limited to, phenyl, 1-naphthyl (bicyclic), 2-naphthyl (bicyclic), anthracenyl (tricyclic), phenanthrenyl (tricyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include, but are not limited to, benzodioxanyl, benzodioxolyl, chromanyl, indolinyl groups, and the like.

As used herein, "heteroaryl" refers to an aromatic monocyclic ring system containing at least 1 ring heteroatom selected from oxygen (O), nitrogen (N) and sulfur (S) or a polycyclic ring system where at least one of the rings present in the ring system is aromatic and contains at least 1 ring heteroatom. Polycyclic heteroaryl groups include two or more heteroaryl rings fused together and monocyclic heteroaryl rings fused to one or more aromatic carbocyclic rings, non-aromatic carbocyclic rings, and/or non-aromatic cycloheteroalkyl rings. A heteroaryl group, as a whole, can have, for example, from 5 to 14 ring atoms and contain 1-5 ring heteroatoms. The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5-membered monocyclic and 5-6 bicyclic ring systems shown below:

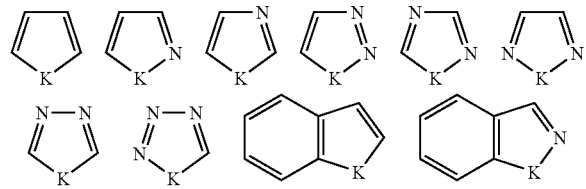

-continued

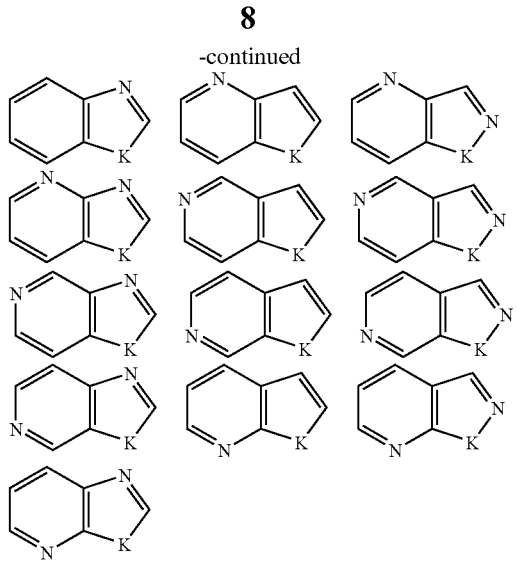

where K is O, S, NH, N-alkyl, N-aryl, or N-(arylalkyl) (e.g., N-benzyl). Examples of such heteroaryl rings include, but are not limited to, pyrrole, furan, thiophene, pyridine, pyrimidine, pyridazine, pyrazine, triazole, tetrazole, pyrazole, imidazole, isothiazole, thiazole, thiadiazole, isoxazole, oxazole, oxadiazole, indole, isoindole, benzofuran, benzothiophene, quinoline, 2-methylquinoline, isoquinoline, quinoxaline, quinazoline, benzotriazole, benzimidazole, benzothiazole, benzisothiazole, benzisoxazole, benzoxadiazole, benzoxazole, cinnoline, 1H-indazole, 2H-indazole, indolizine, isobenzofuran, naphthyridine, phthalazine, pteridine, purine, oxazolopyridine, thiazolopyridine, imidazopyridine, furopyridine, thienopyridine, pyridopyrimidine, pyridopyrazine, pyridopyridazine, thienothiazole, thienoxazole, and thienoimidazole. Further examples of heteroaryl groups include, but are not limited to, 4,5,6,7-tetrahydroindole, tetrahydroquinoline, benzothienopyridine, benzofuropyridine, and the like.

Compounds of the present teachings can include a "divalent group" defined herein as a linking group capable of forming a covalent bond with two other moieties. For example, compounds of the present teachings can include a divalent $C_{1-20}$ alkyl group, such as, for example, a methylene group.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halide (e.g., Cl, Br, I), tosylate (toluenesulfonyl group, TsO), mesylate (methanesulfonyl group, MsO), brosylate (p-bromobenzenesulfonyl group, BsO), nosylate (4-nitrobenzenesulfonyl group, NsO), water ($H_2O$), ammonia ($NH_3$), and triflate (trifluoromethanesulfonyl group, OTf).

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_{1}$-$C_6$, $C_{1}$-$C_5$, $C_{1}$-$C_4$, $C_{1}$-$C_3$, $C_{1}$-$C_2$, $C_{2}$-$C_6$, $C_{2}$-$C_5$, $C_{2}$-$C_4$, $C_{2}$-$C_3$, $C_{3}$-$C_6$, $C_{3}$-$C_5$, $C_{3}$-$C_4$, $C_{4}$-$C_6$, $C_{4}$-$C_5$, and $C_{5}$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19 and 20.

Throughout the specification, structures may or may not be presented with chemical names. Where any question arises as to nomenclature, the structure prevails.

One aspect of the present teachings provides a dimeric compound having the formula:

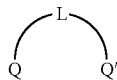

wherein Q and Q' are covalently linked by a linker moiety L.

More specifically, Q and Q' are independently a fused ring tetracarboxylic imide, and L has the formula of A-B-A' or B-A-B', wherein:

A and A' are independently a divalent $C_{1-20}$ alkyl group, a divalent $C_{1-20}$ haloalkyl group, or a covalent bond; and B and B' are independently —O—, —S—, —S(O)—, —C(O)—, —NR$^a$—, —C(O)NR$^a$—, —NR$^a$C(O)—, —O—(CH$_2$CH$_2$O)$_p$—, —SiR$^a{}_2$, a $C_{6-10}$ cycloalkyl group, a $C_{6-14}$ aryl group, a 5-12 membered cycloheteroalkyl group, a 5-14 membered heteroaryl group, or a covalent bond, wherein:

R$^a$ is H, a $C_{1-6}$ alkyl group, a $C_{6-14}$ aryl group, or a —$C_{1-6}$ alkyl-$C_{6-14}$ aryl group; and p is an integer in the range of 1 to 20.

For the dimeric compounds, the linker moiety L as a whole is generally not a covalent bond, i.e., at least one of A, A', B, and B' is not a covalent bond. In certain embodiments, L can be a symmetrical linker, i.e., A and A' in A-B-A' (or alternatively, B and B' in B-A-B) can be the same. However, unsymmetrical linkers can also be used.

In some embodiments, the dimeric compound can have the formula:

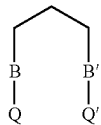

wherein B, B', Q and Q' are as defined herein. For example, B and B' can both be a covalent bond, i.e., the two monomers Q and Q' are linked by a straight chain propyl linker group. In other embodiments, L can be a divalent branched alkyl group, for example, a divalent 2,2-dimethyl propyl group, or a divalent haloalkyl group, for example a divalent 2,2-difluoropropyl group. In other embodiments, B and B' can be a heteroatom-containing group, or a cyclic moiety as described herein.

The monomers Q and Q' can have various fused ring cores including, but not limited to, various rylenes, acenes, and other highly π-conjugated fused ring systems. These fused ring cores can be unsubstituted or substituted, e.g., in the bay position and/or in the terminal position. In particular embodiments, Q and Q' can independently have the formula of:

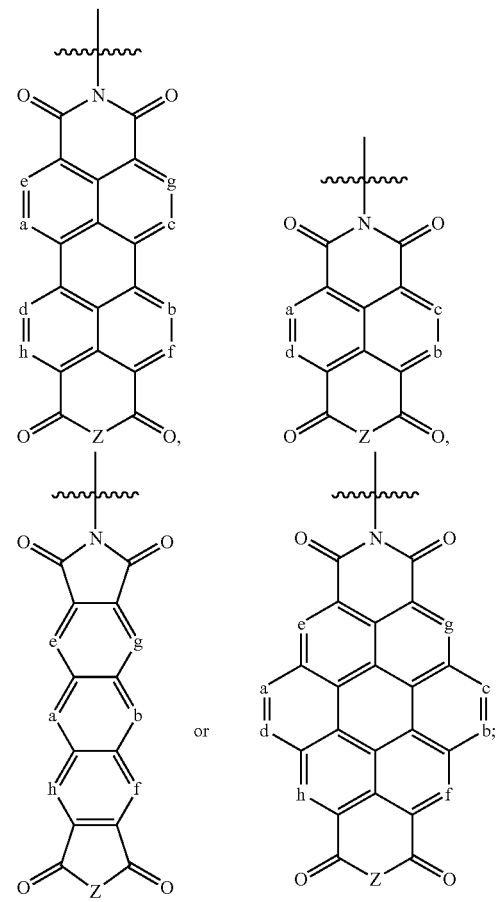

wherein:

Z, at each occurrence, is independently O, S, S(O), NR$^b$, C(O), SiR$^c$R$^d$ or CR$^c$R$^d$, wherein:

R$^b$ is a) H, b) —C(O)$_m$OR$^e$, c) —C(O)$_m$R$^f$, d) —C(O)NR$^f$R$^g$, e) —C(S)OR$^e$, f) —C(S)R$^f$, g) —C(S)NR$^f$R$^g$, h) —S(O)$_m$R$^f$, i) —S(O)$_m$OR$^f$, j) a $C_{1-20}$ alkyl group, k) a $C_{2-20}$ alkenyl group, l) a $C_{2-20}$ alkynyl group, m) a —Y—$C_{3-10}$ cycloalkyl group, n) a —Y—$C_{6-14}$ aryl group, o) a —Y-3-12 membered cycloheteroalkyl group, or p) a —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group is optionally substituted with 1-4 R$^h$ groups;

R$^c$ and R$^d$ are independently a) H, b) a halogen, c) —CH$_2$CH$_2$O)$_q$H, d) —CH$_2$CH$_2$O)$_q$—CH$_3$, e) a $C_{1-20}$ alkoxyl group, f) a $C_{1-20}$ alkyl group, g) a $C_{2-20}$ alkenyl group, h) a $C_{2-20}$ alkynyl group, i) a —Y—$C_{3-10}$ cycloalkyl group, j) a —Y—$C_{6-14}$ aryl group, k) a —Y-3-12 membered cycloheteroalkyl group, or l) a —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group is optionally substituted with 1-4 R$^h$ groups;

R$^e$ is a) H, b) —C(O)R$^f$, c) —C(O)NR$^f$R$^g$, d) —C(S)R$^f$, e) —C(S)NR$^f$R$^g$, f) a $C_{1-20}$ alkyl group, g) a $C_{2-20}$ alkenyl group, h) a $C_{2-20}$ alkynyl group, i) a $C_{3-10}$ cycloalkyl group, j) a $C_{6-14}$ aryl group, k) a 3-12 membered cycloheteroalkyl group, or l) a 5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group is optionally substituted with 1-4 $R^h$ groups;

$R^f$ and $R^g$, at each occurrence, are independently a) H, b) —OH, c) —SH, d) —S(O)$_2$OH, e) —C(O)OH, f) —C(O)NH$_2$, g) —C(S)NH$_2$, h) —OC$_{2-10}$ alkyl, i) —C(O)—C$_{1-20}$ alkyl, j) —C(O)—OC$_{1-20}$ alkyl, k) —C(S)N(C$_{1-20}$ alkyl)$_2$, l) —C(S)NH—C$_{1-20}$ alkyl, m) —C(O)NH—C$_{1-20}$ alkyl, n) —C(O)N(C$_{1-20}$ alkyl)$_2$, o) —S(O)$_m$—C$_{1-20}$ alkyl, p) —S(O)$_m$—OC$_{1-20}$ alkyl, q) a $C_{1-20}$ alkyl group, r) a $C_{2-20}$ alkenyl group, s) a $C_{2-20}$ alkynyl group, t) a $C_{1-20}$ alkoxy group, u) a $C_{3-10}$ cycloalkyl group, v) a $C_{6-14}$ aryl group, w) a 3-12 membered cycloheteroalkyl group, or x) a 5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, the 5-14 membered heteroaryl group is optionally substituted with 1-4 $R^h$ groups;

$R^h$, at each occurrence, is independently a) a halogen, b) —CN, c) —NO$_2$, d) oxo, e) —OR$^i$, f) —SR$^i$, g) —NR$^i$R$^j$, h) —N(O)R$^i$R$^j$, i) —S(O)$_m$R$^i$, j) —S(O)$_m$OR$^i$, k) —S(O)$_m$NR$^i$R$^j$, l) —C(O)R$^i$, m) —C(O)OR$^i$, n) —C(O)NR$^i$R$^j$, o) —C(S)NR$^i$R$^j$, p) SiH$_3$, q) SiH(C$_{1-20}$ alkyl)$_2$, r) SiH$_2$(C$_{1-20}$ alkyl), s) Si(C$_{1-20}$ alkyl)$_3$, t) a $C_{1-20}$ alkyl group, u) a $C_{2-20}$ alkenyl group, v) a $C_{2-20}$ alkynyl group, w) a —Y—C$_{3-10}$ cycloalkyl group, x) a —Y—C$_{6-14}$ aryl group, y) a —Y-3-12 membered cycloheteroalkyl group, or z) a —Y-5-14 membered heteroaryl group, each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group; and the 5-14 membered heteroaryl group is optionally substituted with 1-4 $R^k$ groups;

$R^i$ and $R^j$, at each occurrence, are independently a) H, b) —S(O)$_2$OH, c) —C(O)OH, d) —C(O)NH$_2$, e) —C(S)NH$_2$, f) —C(O)—C$_{1-20}$ alkyl, g) —C(O)—OC$_{1-20}$ alkyl, h) —C(S)N(C$_{1-20}$ alkyl)$_2$, i) —C(S)NH—C$_{1-20}$ alkyl, j) —C(O)NH—C$_{1-20}$ alkyl, k) —C(O)N(C$_{1-20}$ alkyl)$_2$, l) —S(O)$_m$—C$_{1-20}$ alkyl, m) —S(O)$_m$—OC$_{1-20}$ alkyl, n) —C(O)—C$_{6-14}$ aryl, o) —C(O)—OC$_{6-14}$ aryl, p) —C(S)N(C$_{6-14}$ aryl)$_2$, q) —C(S)N(C$_{1-20}$ alkyl)-C$_{6-14}$ aryl, r) —C(S)NH—C$_{6-14}$ aryl, s) —C(O)NH—C$_{6-14}$ aryl, t) —C(O)N(C$_{1-20}$ alkyl)-C$_{6-14}$ aryl, u) —C(O)N(C$_{6-14}$ aryl)$_2$, v) —S(O)$_m$—C$_{6-14}$ aryl, w) —S(O)$_m$—OC$_{6-14}$ aryl, x) a $C_{1-20}$ alkyl group, y) a $C_{2-20}$ alkenyl group, z) a $C_{2-20}$ alkynyl group, aa) a $C_{1-20}$ alkoxy group, ab) a $C_{3-10}$ cycloalkyl group, ac) a $C_{6-14}$ aryl group, ad) a 3-12 membered cycloheteroalkyl group, or ae) a 5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group is optionally substituted with 1-4 $R^k$ groups;

$R^k$, at each occurrence, is independently a) a halogen, b) —CN, c) —N$_2$, d) oxo, e) —OH f) —NH$_2$, g) —NH(C$_{1-20}$ alkyl), h) —N(C$_{1-20}$ alkyl)$_2$, i) —N(C$_{1-20}$ alkyl)-C$_{6-14}$ aryl, j) —N(C$_{6-14}$ aryl)$_2$, k) —S(O)$_m$H, l) —S(O)$_m$—C$_{1-20}$ alkyl, m) —S(O)$_2$OH, n) —S(O)$_m$—OC$_{1-20}$ alkyl, o) —S(O)$_m$—OC$_{6-14}$ aryl, p) —CHO, q) —C(O)—C$_{1-20}$ alkyl, r) —C(O)—C$_{6-14}$ aryl, s) —C(O)OH, t) —C(O)—OC$_{1-20}$ alkyl, u) —C(O)OC$_{6-14}$ aryl, v) —C(O)NH$_2$, w) —C(O)NH—C$_{1-20}$ alkyl, x) —C(O)N(C$_{1-20}$ alkyl)$_2$, y) —C(O)NH—C$_{6-14}$ aryl, z) —C(O)N(C$_{1-20}$ alkyl)-C$_{6-14}$ aryl, aa) —C(O)N(C$_{6-14}$ aryl)$_2$, ab) —C(S)NH$_2$, ac) —C(S)NH—C$_{1-20}$ alkyl, ad) —C(S)N(C$_{1-20}$ alkyl)$_2$, ae) —C(S)N(C$_{6-14}$ aryl)$_2$, af) —C(S)N(C$_{1-20}$ alkyl)-C$_{6-14}$ aryl, ag) —C(S)NH—C$_{6-14}$ aryl, ah) —S(O)$_m$NH$_2$, ai) —S(O)$_n$NH(C$_{1-20}$ alkyl), aj) —S(O)$_m$N(C$_{1-20}$ alkyl)$_2$, ak) —S(O)$_m$NH(C$_{6-14}$ aryl), al) —S(O)$_m$N(C$_{1-20}$ alkyl)-C$_{6-14}$ aryl, am) —S(O)$_m$N(C$_{6-14}$ aryl)$_2$, an) SiH$_3$, ao) SiH(C$_{1-20}$ alkyl)$_2$, ap) SiH$_2$(C$_{1-20}$ alkyl), ar) —Si(C$_{1-20}$ alkyl)$_3$, as) a $C_{1-20}$ alkyl group, at) a $C_{2-20}$ alkenyl group, au) a $C_{2-20}$ alkynyl group, av) a $C_{1-20}$ alkoxy group, aw) a $C_{1-20}$ alkylthio group, ax) a $C_{1-20}$ haloalkyl group, ay) a $C_{3-10}$ cycloalkyl group, az) a $C_{6-14}$ aryl group, ba) a 3-12 membered cycloheteroalkyl group, or bb) a 5-14 membered heteroaryl group;

Y is a divalent $C_{1-20}$ alkyl group, a divalent $C_{1-20}$ haloalkyl group, or a covalent bond;

m, at each occurrence, is independently 0, 1 or 2; and q is an integer in the range of 1 to 20; and a, b, c, d, e, f, g and h, at each occurrence, are independently CR$^m$, SiR$^m$, N or P, wherein:

$R^m$, at each occurrence, is independently a) H, b) halogen, c) —CN, d) —NO$_2$, e) —OR$^i$, f) —SR$^i$, g) —NR$^i$R$^j$, h) —N(O)R$^i$R$^j$, i) —S(O)$_m$R$^i$, j) —S(O)$_m$OR$^i$, k) —S(O)$_m$NR$^i$R$^j$, l) —C(O)R$^i$, m) —C(O)OR$^i$, n) —C(O)NR$^i$R$^j$, o) —C(S)NR$^i$R$^j$, p) SiH$_3$, q) SiH(C$_{1-20}$ alkyl)$_2$, r) SiH$_2$(C$_{1-20}$ alkyl), s) Si(C$_{1-20}$ alkyl)$_3$, t) a $C_{1-20}$ alkyl group, u) a $C_{2-20}$ alkenyl group, v) a $C_{2-20}$ alkynyl group, w) a $C_{1-20}$ haloalkyl group, x) a —Y—C$_{3-10}$ cycloalkyl group, y) a —Y—C$_{6-14}$ aryl group, z) a —Y-3-12 membered cycloheteroalkyl group, or aa) a —Y-5-14 membered heteroaryl group, wherein each of the $C_{1-20}$ alkyl group, the $C_{2-20}$ alkenyl group, the $C_{2-20}$ alkynyl group, the $C_{3-10}$ cycloalkyl group, the $C_{6-14}$ aryl group, the 3-12 membered cycloheteroalkyl group, and the 5-14 membered heteroaryl group is optionally substituted with 1-4 $R^k$ groups; and Y, $R^i$, $R^j$, $R^k$ and m are as defined above.

In certain embodiments, a, b, c, d, e, f, g and h, at each occurrence, can be independently CR$^m$, N or P, where $R^m$ is as defined herein. For example, each of a, b, c, d, e, f, g and h can be CR$^m$, and $R^m$, at each occurrence, can be independently H, —CN, —OR$^i$, a halogen, a $C_{1-20}$ haloalkyl group, or a 3-12 membered cycloheteroalkyl group, wherein the 3-12 membered cycloheteroalkyl group can be optionally substituted with 1-4 $R^k$ groups, and $R^i$ and $R^k$ are as defined herein. More specifically, each of a, b, c and d can be CR$^m$, where $R^m$, at each occurrence, can be independently H, Br, Cl, —CN, CF$_3$, N-pyrrolidine, or a 3,5-di-tert-butylphenoxyl group. In particular embodiments, Q and Q' can independently have the formula:

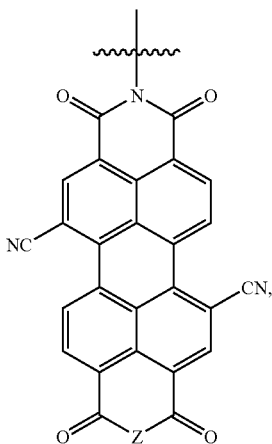

where Z is as defined herein.

In some embodiments, Q and Q' can be a fused ring tetracarboxylic diimide, that is, Z, in each of the formulae of Q and Q' provided herein, can be $NR^b$, where $R^b$ is a $C_{1-20}$ alkyl group, a $C_{1-20}$ haloalkyl group, a $C_{2-20}$ alkenyl group, a $C_{3-10}$ cycloalkyl group, a $C_{6-14}$ aryl group, or a 3-12 membered cycloheteroalkyl group, each of which can be optionally substituted with 1-4 $R^h$ groups. For example, $R^b$ can be a straight chain $C_{1-20}$ alkyl group, a branched $C_{3-20}$ alkyl group, a $C_{4-20}$ alkenyl group, a $C_{1-20}$ fluoroalkyl group, a $C_{3-10}$ cycloalkyl group, a —Y—$C_{6-14}$ aryl group, or a 3-12 membered cycloheteroalkyl group, wherein the $C_{6-14}$ aryl group and the 3-12 membered cycloheteroalkyl group can be optionally substituted with 1-4 $R^h$ groups, and Y is as defined herein. In particular embodiments, $R^b$ can be —$C_8H_{17}$, —$C_{12}H_{25}$, —$CH(C_6H_{13})_2$, —$CH(C_{11}H_{23})_2$, —$CH_2C_3F_7$, —$CH_2C_7F_{15}$, a cyclohexyl group, a benzyl group, a 4-butyl benzyl group, a 2,3,4,5,6-pentafluorophenyl group, or a 3,4,5-tris(dodecyloxy)phenyl group.

In another aspect, the present teachings provide a polymeric compound that includes a polyalkylene backbone or a substituted polyalkylene backbone. More specifically, one or more repeating units of the polymeric compound can include a pendant group having the formula L-Q, where L and Q are as defined above. In some embodiments, the linker L can be a covalent bond.

In certain embodiments, the polyalkylene backbone or the substituted polyalkylene backbone can be polyethylene, polypropylene, polystyrene, polyphenol, polyvinylalcohol, polyacrylate, or a copolymer thereof.

In some embodiments, such polymeric compounds can be a homopolymer having only repeating units of L-Q. In other embodiments, such polymeric compounds can be a copolymer having repeating units of L-Q and L'-Q'. Respectively, these embodiments can be represented by the formulae:

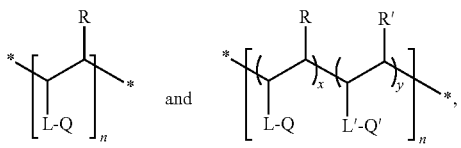

wherein:
Q and L are as defined above;
R and R' are independently H, OH, —C(O)OH, a $C_{1-6}$ alkyl group, a phenyl group, or a phenol group;
Q' is a fused-ring tetracarboxylic imide;
L' has the formula A-B-A' or B-A-B', wherein:
A and A' are independently a divalent $C_{1-20}$ alkyl group, a divalent $C_{1-20}$ haloalkyl group, or a covalent bond; and
B and B' are independently —O—, —S—, —S(O)—, —C(O)—, —$NR^a$—, —C(O)$NR^a$—, —$NR^aC(O)$—, —O—$(CH_2CH_2O)_p$—, —$SiR^a_2$—, a $C_{6-10}$ cycloalkyl group, a $C_{6-14}$ aryl group, a 5-12 membered cycloheteroalkyl group, a 5-14 membered heteroaryl group, or a covalent bond, wherein:
$R^a$ is H, a $C_{1-6}$ alkyl group, a $C_{6-14}$ aryl group, or a —$C_{1-6}$ alkyl-$C_{6-14}$ aryl group;
p is an integer in the range of 1 to 20;
n is an integer from 3 to 1,000,000; and
x+y=1, wherein x>0 and y>0.

In a further aspect, the present teachings provide a copolymeric compound that includes at least two types of repeating units, one of which includes the pendant group L-Q, where L and Q are as defined herein. The other repeating unit can be an alkylene, a substituted alkylene, and a heteroalkylene that does not include the pendant group L-Q. These copolymeric compounds can be represented by the formula:

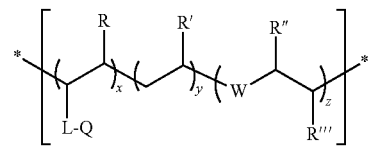

wherein:
R, R', R" and R'" are independently H, OH, —C(O)OH, a $C_{1-6}$ alkyl group, a phenyl group, or a phenol group;
W is O, S, $NR^1$, $CR^2R^3$, or $SiR^2R^3$, where $R^1$ is H, a $C_{1-20}$ alkyl group, or $C_{1-20}$ haloalkyl group; and $R^2$ and $R^3$ are independently H, a halogen, a $C_{1-20}$ alkyl group, or $C_{1-20}$ haloalkyl group; and
x+y+z=1, where 0<x<1, y≧0, and z≧0.

Many of the compounds disclosed herein have satisfactory solubility in common organic solvents, making them suitable for use in various solution-phase processes. Examples of common organic solvents include, but are not limited to, petroleum ethers; aromatic hydrocarbons such as benzene, toluene, xylene, and mesitylene; ketones, such as acetone, and 2-butanone; ethers, such as tetrahydrofuran and diethyl ether; alcohols, such as isopropyl alcohol; aliphatic hydrocarbons, such as hexanes; acetates, such as ethyl acetate; and halogenated aliphatic hydrocarbons, such as dichloromethane, chloroform, and ethylene chloride. As used herein, a compound can be considered soluble in a solvent when at least 1 mg of the compound is soluble in 1 mL of the solvent.

Various solution processing techniques have been used with organic electronics. For example, much of the printed electronics technology has focused on inkjet printing, primarily because this technique offers greater control over feature position and multilayer registration. Inkjet printing is a non-contact process, which offers the benefits of not requiring a preformed master (compared to contact printing techniques), as well as digital control of ink ejection, thereby providing drop-on-demand printing. However, contact printing techniques have the key advantage of being well-suited for very fast roll-to-roll processing. Exemplary contact printing techniques include, but are not limited to screen-printing, gravure, offset, and microcontact printing.

The fundamental parameters controlling printing quality are the rheological properties of the inks and the chemical characteristics, mainly those affecting the surface energy, of the material on which the ink is deposited. When the ink wets the substrate, how the pattern forms on the substrate surface depends, in large part, on the physical and chemical interaction between molecules of the ink and the material. For example, the wetting contact angle determines the spread of a liquid drop on the surface and depends on the relative surface energy of the solid-liquid, solid-vapor, and liquid-vapor interfaces. For organic inks, high-energy surfaces result in a small contact angle and considerable substrate wetting, while a low substrate surface energy results in greatly reduced ink droplet footprint. The surface energy and contact angle also relate to the adhesion of the liquid to the surface. Strong adhesion is associated with wetting and low adhesion with large contact angles.

Small molecule-based inks such as those of simple PDI and NDI derivatives generally are well suited for inkjet printing since low viscosity inks can be used. However, contact printing techniques can offer higher printing speed, and to date, the use of contact printing with organic electronics has been limited by the lack of high-viscosity formulations of organic electronic inks. Solubility requirements can also differ for contact and noncontact printing techniques. For noncontact printing techniques such as inkjet printing, the solubility requirement is generally less stringent and a solubility range as low as about 1-4 mg/mL can suffice. For gravure printing, a higher solubility range may be necessary, often in the range of about 50-100 mg/mL. Other contact printing techniques such as screen-printing and flexo printing, can require even higher solubility ranges, e.g., about 100-1000 mg/mL.

Without wishing to be bound to any particular theory, it is believed that the general molecular design approach of attaching a small molecule n-type organic semiconducting compound to a linker and/or a polymeric backbone such as those disclosed herein affords the ability to control and vary the solution viscosity of such organic semiconducting compounds when dissolved in a solvent. As the intrinsic viscosity of a molecule is generally proportional to its molecular weight, the solution viscosities of the oligomeric and polymeric versions of a small molecule compound can be expected to be higher than that of the unmodified small molecule.

However, other factors, such as the shape and the rigidity of the linker and the polymeric chain, also can affect the intrinsic viscosity of the oligomers and polymers. Accordingly, the choice of the linkers and the polymeric backbone can be affected by considerations such as the intermolecular and intramolecular ordering of the semiconductor materials disclosed herein. For example, efficient perylene unit core-core stacking is known to be a prerequisite for efficient charge transport π-π core stacking can occur intermolecularly and intramolecularly. Without wishing to be bound to any particular theory, the optimal distance for efficient charge hopping between aromatic units has been determined to be between about 3.2-3.5 Å. Accordingly, linkers and polymeric backbones that can lead to a molecular arrangement having such an intermolecular and/or intramolecular distance can be advantageous, which was observed with an optionally substituted propyl linker in the dimer embodiment, and an optionally substituted polyethylene backbone in the polymer embodiment of the present teachings.

Monomer precursors, before reacting with the linker L or the polymeric backbone to form the dimeric and polymeric compounds disclosed herein, generally have somewhat different chemical structures compared to Q and Q'. In particular, the monomer precursors can include different functional groups at their terminal ends. For example, these monomer precursors can be fused ring tetracarboxylic acids, dianhydrides, and other derivatives. Exemplary monomer precursors that can be used to prepare the dimeric and polymeric compounds of the present teachings include, but are not limited to the following:

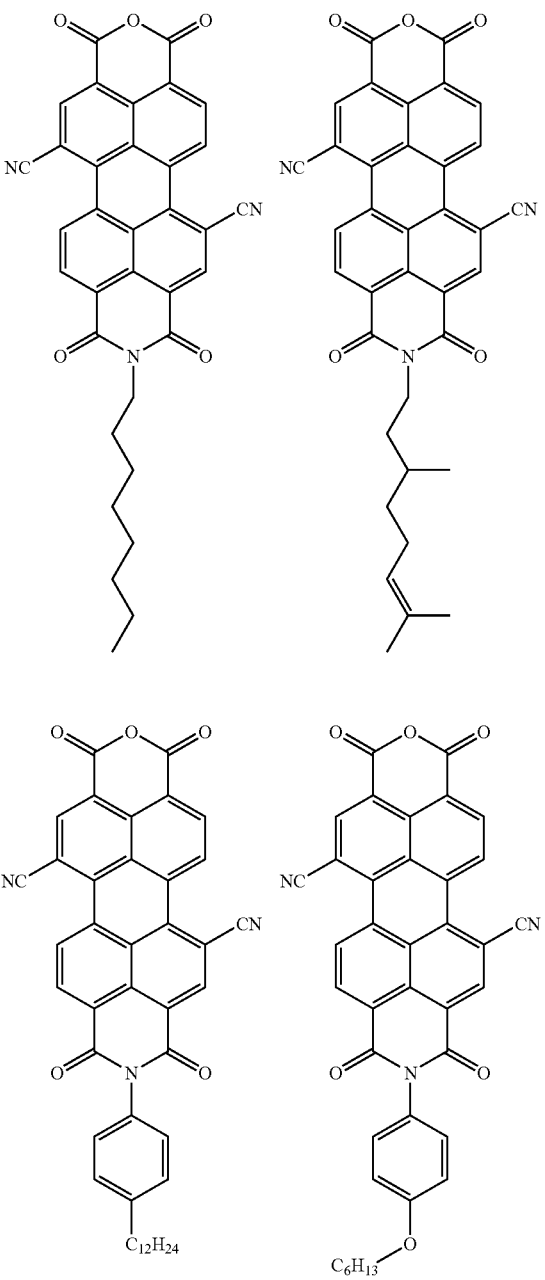

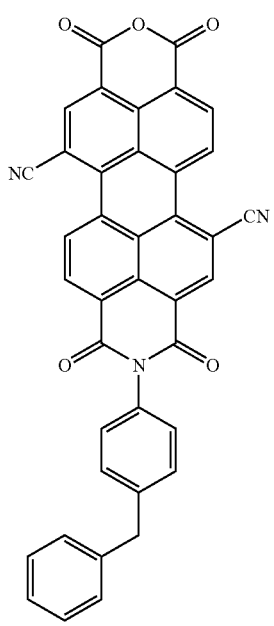
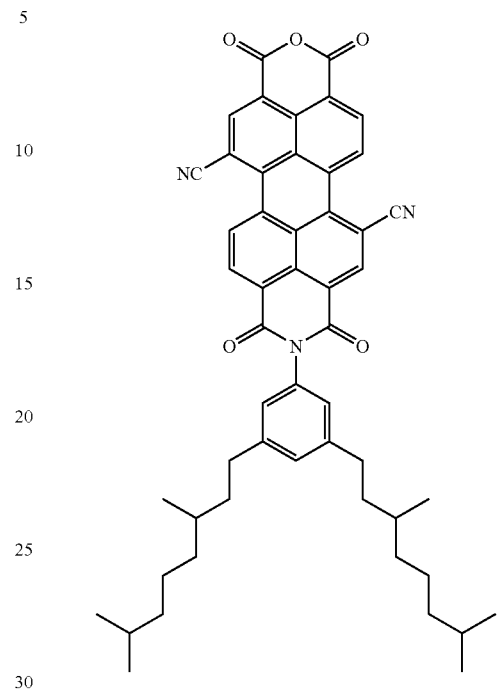
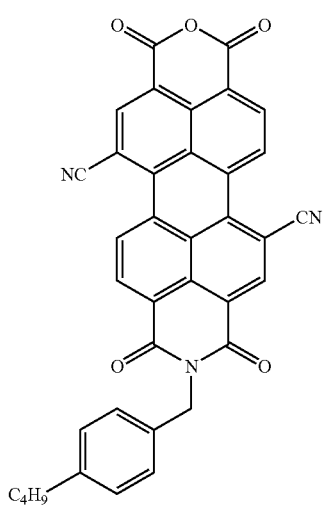
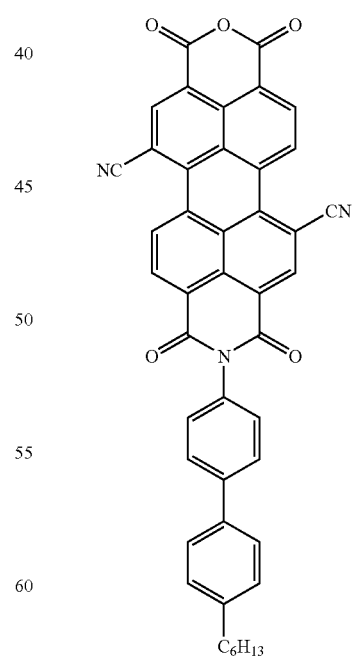

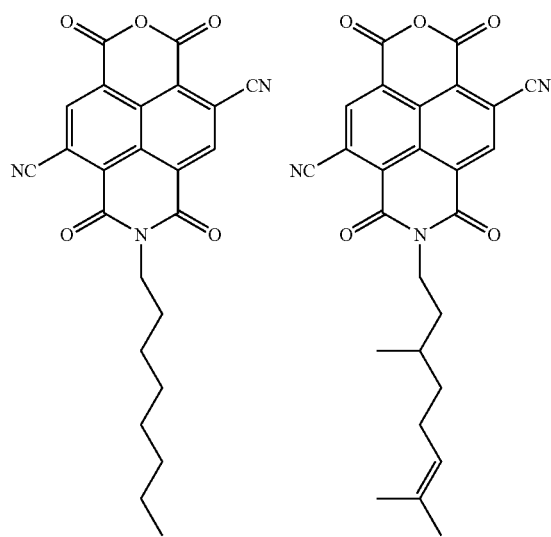
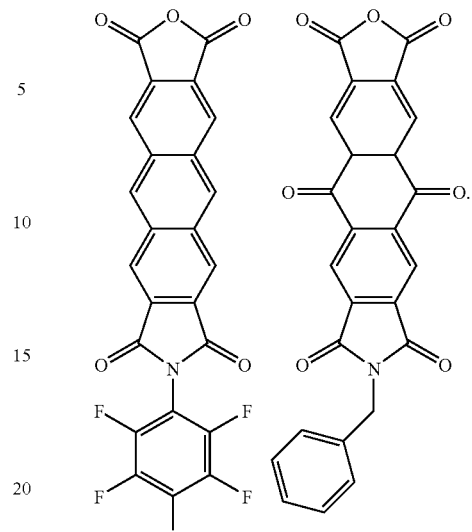
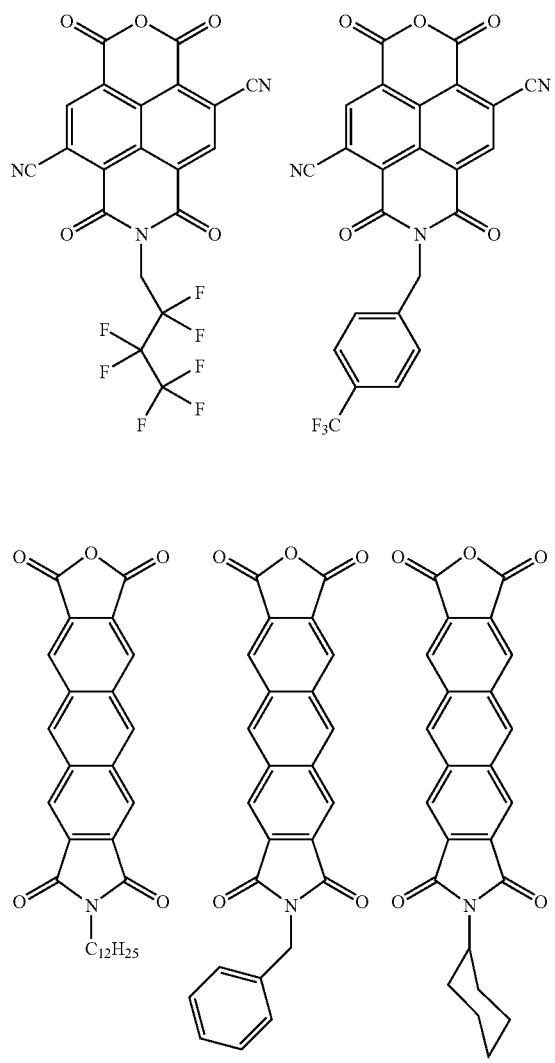
Compounds of the present teachings can be prepared following three general synthetic routes illustrated in Scheme 1 below.
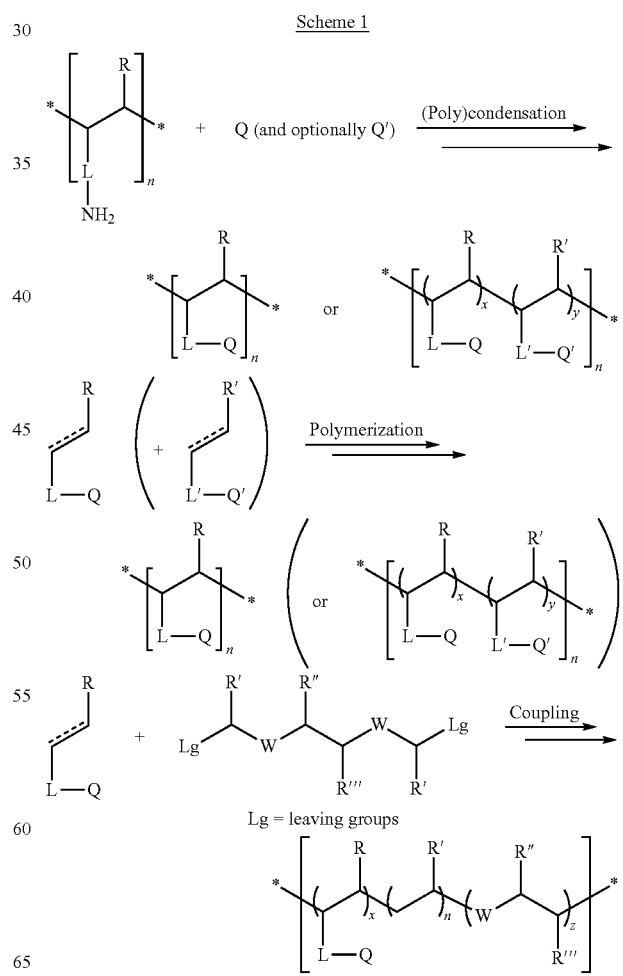

In the first approach a (poly)amine-substituted polymeric backbone is reacted with Q (and optionally Q') affording the corresponding oligomer and polymeric species. In the second approach, L-Q is attached to a polymerizable group and subsequent polymerization is initiated to provide the corresponding polymeric species. In the third approach, well-established coupling reactions can be used to copolymerize the L-Q-containing moiety with a second polymer.

The present teachings further provide compositions that include the compounds disclosed herein dissolved in an organic solvent. Various articles of manufacture, such as thin film semiconductors, organic field effect transistors, complementary metal oxide semiconductors (CMOS), complementary inverters, D flip-flops, and ring oscillators, that make use of the organic semiconducting compounds disclosed herein are also with the scope of the present teachings.

The following examples are provided to illustrate further and to facilitate the understanding of the present teachings and are not in any way intended to limit the invention.

Unless otherwise noted, all reagents were purchased from commercial sources and used without further purification. Anhydrous tetrahydrofuran (THF) was distilled from sodium/benzophenone. Conventional Schlenk techniques were used, and reactions were carried out under nitrogen unless otherwise noted. UV-vis spectra were recorded on a Cary Model 1 UV-vis spectrophotometer. Fluorescent measurements were recorded on a Photon Technology International model QM-2 fluorimeter. NMR spectra were recorded on a Varian Unity Plus 500 spectrometer ($^1$H, 500 MHz; $^{13}$C, 125 MHz). Electrospray mass spectrometry was performed with a Thermo Finnegan model LCQ Advantage mass spectrometer.

Example 1

Preparation of N-(1-hexylheptyl)perylene-3,4,9,10-tetracarboxylic-3,4-anhydride-9,10-imide Scheme 2 below illustrates an exemplary synthetic route for preparing a monomer precursor that can be used in accordance with the present teachings.

Scheme 2

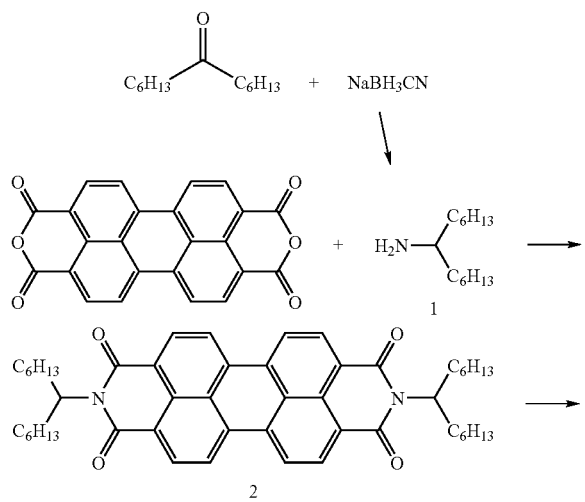

-continued

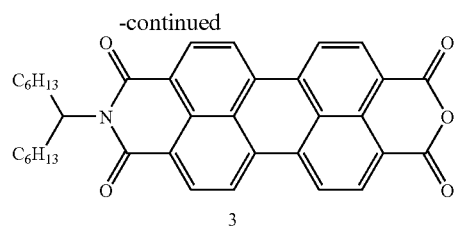

3

Preparation of 1-hexylheptylamine 1

In a 250 mL round bottom flask, 5.00 g (25.5 mmol) dihexylketone, 19.7 g (255 mmol) ammonium acetate, and 1.10 g (17.8 mmol) sodium cyanoborohydride (NaBH$_3$CN) were dissolved in 75 mL absolute MeOH and stirred at room temperature for 48 hours, until no significant amount of the starting material could be detected by NMR. The mixture was quenched by adding concentrated hydrochloric acid (HCl) dropwise (~3 mL), then concentrated in vacuo. The resulting white solid was taken up in 500 mL water, basified to pH 10 with solid potassium hydroxide (KOH), and extracted with chloroform (CHCl$_3$) twice (200 mL each). The CHCl$_3$ fractions were combined and concentrated to give 4.12 g (81%) of 1-hexylheptylamine 1 as a pale yellow oil. $^1$H NMR (D$_2$O, 500 MHz): δ 0.73 (t, 6H), 1.15-1.23 (m, 16H), 1.55 (m, 4H), 3.13 (m, 1H).

Preparation of N,N'-bis(1-hexylheptyl)perylene-3,4,9,10-tetracarboxylic diimide 2

In a 500 mL round bottom flask, 2.0 g (5.5 mmol) perylene-3,4,9,10-tetracarboxylic dianhydride and 2.6 g (13.5 mmol) of compound 1 in imidazole (9 g) were stirred for 5 hours at 180° C. The reaction mixture was cooled to room temperature, taken up in 100 mL of ethanol, treated with 400 mL of HCl (2M), and stirred overnight. The dark red precipitate was filtered and rinsed thoroughly with water, and dried at 130° C. to give 3.5 g (84%) of N,N'-bis(1-hexylheptyl)perylene-3,4,9,10-tetracarboxylic diimide 2 as a black solid. $^1$H NMR (CHCl$_3$, 500 MHz): δ 0.83 (t, 12H), 1.18-1.30 (m, 32H), 1.84 (m, 4H), 2.25 (m, 4H), 5.19 (m, 2H), 8.63-8.68 (m, 8H).

Preparation of N-(1-hexylheptyl)perylene-3,4,9,10-tetracarboxylic-3,4-anhydride-9,10-imide 3

In a 250 mL round bottom flask 3.45 g (4.57 mmol) of compound 2 was suspended in 85 mL tert-butanol and treated with 860 mg (15.3 mmol) of 85% solid KOH. The reaction mixture was heated to reflux and vigorously stirred for 45 minutes. The mixture was cooled, treated with 80 mL of acetic acid and 40 mL of 2M HCl, and stirred overnight. The black precipitate was filtered, washed with distilled water, and dried at 130° C. This solid was suspended in 150 mL of 10% potassium carbonate (K$_2$CO$_3$) solution and heated to reflux for 30 minutes. The mixture is cooled and filtered. The filter cake was rinsed with warm 10% K$_2$CO$_3$ until the filtrate was clear, rinsed twice with 100 mL of 2M HCl, then rinsed thoroughly with water and dried at 130° C. The dry solid was suspended in 100 mL of boiling water, and triethylamine (TEA) was added until a dark purple solution of the desired product formed. The remaining starting material was filtered off and the dark purple filtrate was acidified with 3 volumes of 2M HCl, and stirred overnight. The resulting dark red precipitate was filtered, rinsed thoroughly with water, and dried at 130° C. This material was similarly treated once more with water/TEA to remove remaining traces of the starting material. The purple/dark red solutions, upon precipitation and drying, together yielded 0.9 g (34%) of N-(1-hexylheptyl) perylene-3,4,9,10-tetracarboxylic-3,4-anhydride-9,10-imide 3 as a black solid. $^1$H NMR (CHCl$_3$, 500 MHz): δ 0.73 (t, 6H), 1.09-1.22 (m, 16H), 1.76 (m, 2H), 2.13 (m, 2H), 5.15 (m, 1H), 8.59 (dd, 8H).

Example 2

Preparation of N-(1-hexylheptyl)perylene-3,4,9,10-tetracarboxylic-3,4-anhydride-9,10-imide dimer 4

Scheme 3 below illustrates an exemplary synthetic route for the preparation of N-(1-hexylheptyl)perylene-3,4,9,10-tetracarboxylic-3,4-anhydride-9,10-imide dimer 4.

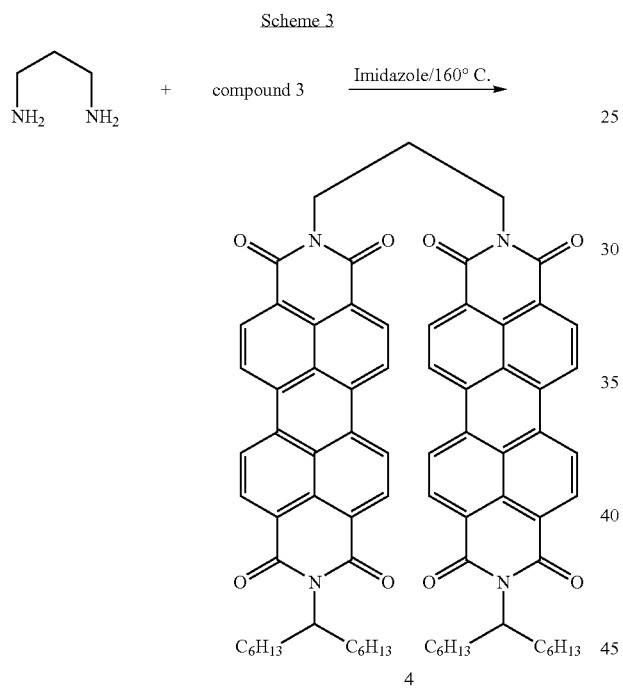

In a 50 mL round bottom flask, N-(1-hexylheptyl) perylene-3,4,9,10-tetracarboxylic-3,4-anhydride-9,10-imide 3 (400 mg, 0.69 mmol) and 1,3-diaminopropane (23 μL, 0.27 mmol) were dissolved in imidazole (2.5 g) and stirred for 6 hours at 180° C. The reaction mixture was cooled, suspended in 5 mL of ethanol (EtOH), then treated with 40 mL of 2M HCl and stirred overnight. The black precipitate was filtered and dried at 130° C. to give N-(1-hexylheptyl)perylene-3,4,9,10-tetracarboxylic-3,4-anhydride-9,10-imide dimer 4 as a black solid (315 mg, 39%). $^1$H NMR (CHCl$_3$, 500 MHz): δ 0.84 (t, 12H), 1.24 (m, 24H), 1.34 (m, 8H), 1.89 (m, 4H), 2.26 (m, 4H), 2.37 (m, 2H), 4.43 (s, 4H), 5.18 (m, 2H), 8.53-8.61 (dd, 16H); $^{13}$C NMR (CHCl$_3$, 500 MHz): δ 163.37, 134.53, 134.12, 131.77, 131.34, 131.04, 129.51, 129.25, 126.23, 124.20, 123.45, 123.08, 122.85, 55.07, 32.57, 32.01, 29.92, 29.48, 27.23, 26.81, 22.83, 14.29; ESI MS: m/z 1184.3 (M$^+$); Anal: calc. C, 77.95; H, 6.46; N, 4.73. found C, 77.42; H, 6.50; N, 4.52; m.p. 395° C. (DSC).

Example 3

Preparation of N-(1-hexylheptyl)perylene-3,4,9,10-tetracarboxylic-3,4-anhydride-9,10-imide polymer 5

Scheme 4 below illustrates an exemplary synthetic route for the preparation of N-(1-hexylheptyl)perylene-3,4,9,10-tetracarboxylic-3,4-anhydride-9,10-imide polymer-5.

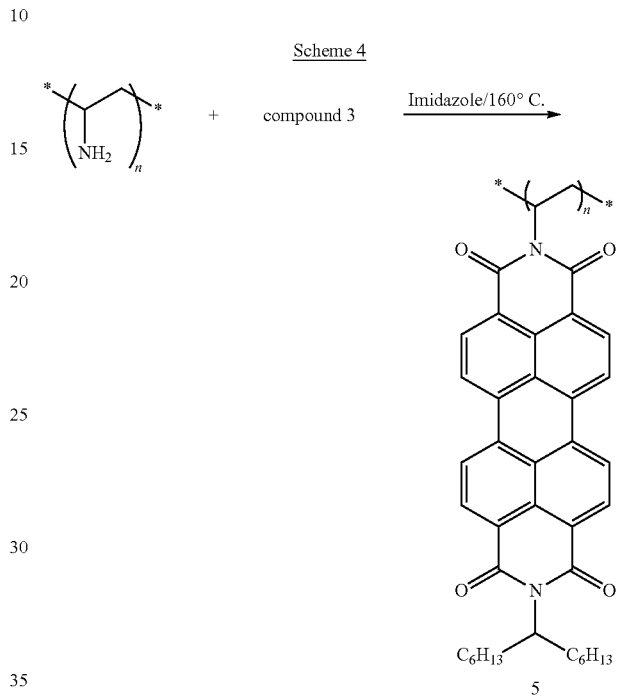

In a 50 mL round bottom flask, N-(1-hexylheptyl) perylene-3,4,9,10-tetracarboxylic-3,4-anhydride-9,10-imide 3 (800 mg, 1.4 mmol) and polyaminoethylene (0.1 mmol) were dissolved in imidazole (3.0 g) and stirred for 3 days at 180° C. The reaction mixture was cooled, added into EtOH (20 mL), then treated with 50 mL of 2M HCl and stirred overnight. The black precipitate was filtered and dried at 130° C. to give the N-(1-hexylheptyl)perylene-3,4,9,10-tetracarboxylic-3,4-anhydride-9,10-imide polymer 5 as a brown solid (160 mg).

Example 4

Optical properties of dimers of N-(1-hexylheptyl) perylene-3,4,9,10-tetracarboxylic-3,4-anhydride-9, 10-imide 4

The N-(1-hexylheptyl)perylene-3,4,9,10-tetracarboxylic-3,4-anhydride-9,10-imide dimer 4 prepared according to the procedure described in Example 2 was dissolved in THF and spin-coated on glass slides as thin films. The surface of the thin films appeared smooth to the naked eye.

FIG. 1 shows the UV-vis absorption spectra of a solution and a thin film sample of the N-(1-hexylheptyl)perylene-3,4, 9,10-tetracarboxylic-3,4-anhydride-9,10-imide dimer 4. In solution, the absorption maxima of the dimer were observed to be located at 523 nm. The thin film samples showed a blue-shifted a absorption maxima, at 496 nm for unannealed thin film and at 462 nm for thin film annealed at 250° C., suggesting that in solid state the dimer achieves a higher degree of molecular organization, namely, crystallinity. The band gaps of the dimer in solution, on glass, and as annealed thin film on glass were estimated to be 2.30, 2.02, and 1.93 eV, respectively, from the UV-vis spectra obtained.

Example 5

Photoluminescence of dimers of N-(1-hexylheptyl) perylene-3,4,9,10-tetracarboxylic-3,4-anhydride-9, 10-imide 4

Figure 2:
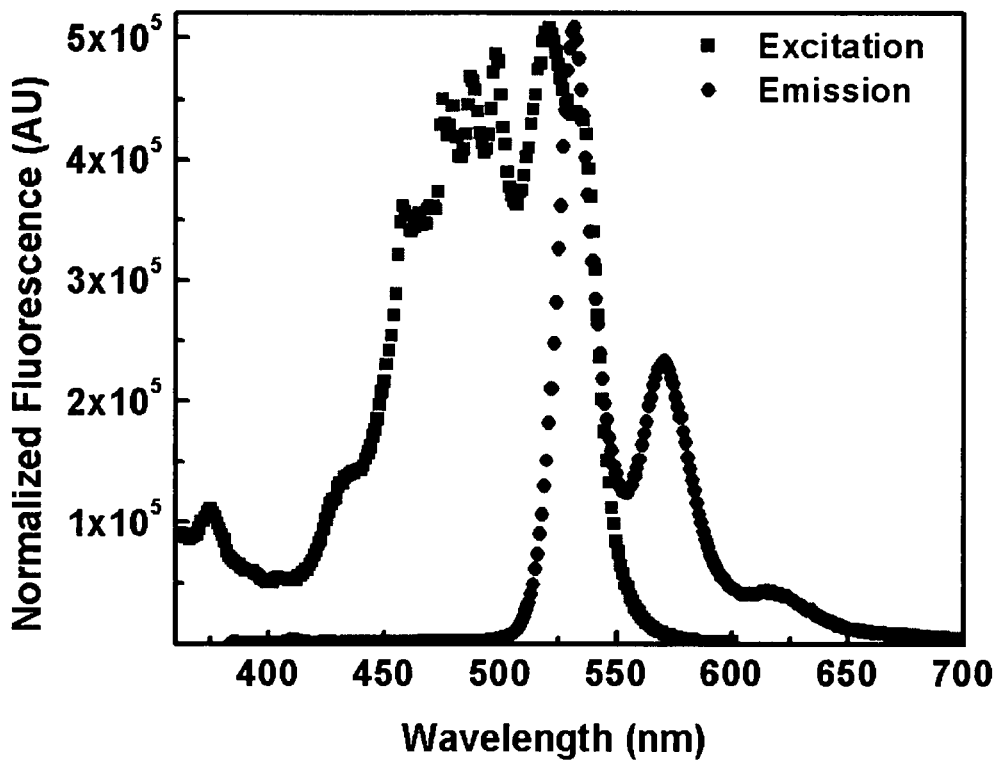
FIG. 2 provides a photoluminescence spectrum of a solution comprising compounds of the present teachings.

FIG. 2 provides a photoluminescence spectrum of a solution of the N-(1-hexylheptyl)perylene-3,4,9,10-tetracarboxylic-3,4-anhydride-9,10-imide dimer 4 in THF.

The spectrum showed two emission maxima at 532 nm and 571 nm, respectively, when the solution was excited at 375 nm.

Example 6

Thermal properties of dimers of N-(1-hexylheptyl) perylene-3,4,9,10-tetracarboxylic-3,4-anhydride-9, 10-imide 4

Figure 3:
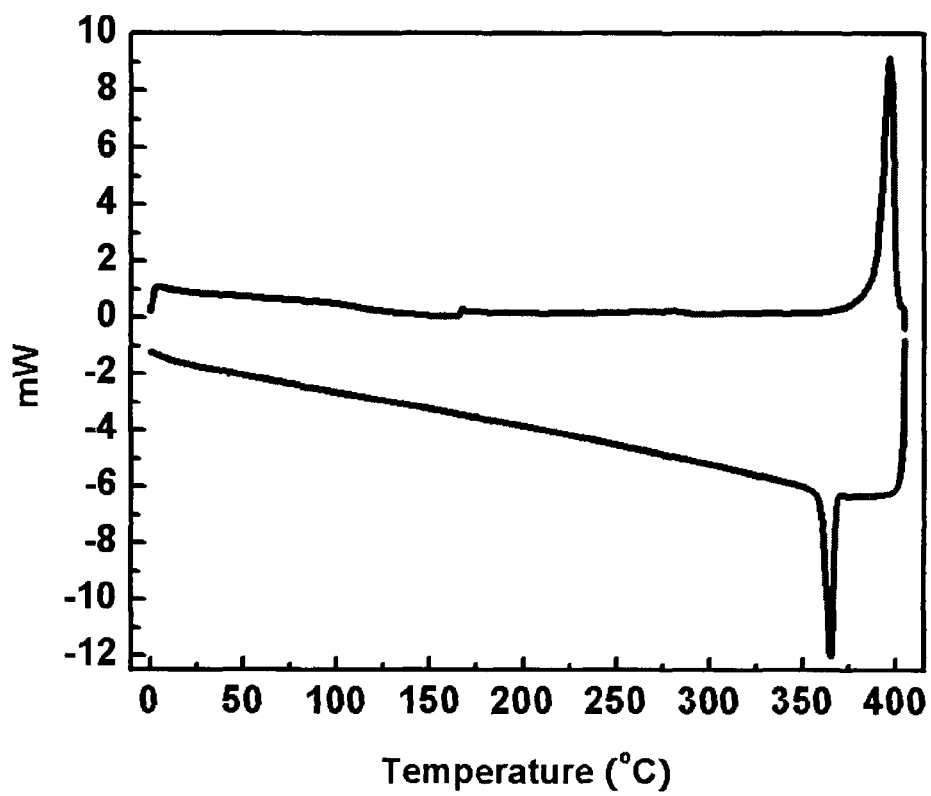
FIG. 3 provides differential scanning calorimetry (DSC) curves obtained from a compound of the present teachings.

The thermal properties of the N-(1-hexylheptyl)perylene-3,4,9,10-tetracarboxylic-3,4-anhydride-9,10-imide dimer 4 were examined by differential scanning calorimetry (FIG. 3). FIG. 3 shows a single endotherm around 395° C. upon heating and a single exotherm at 365° C. upon cooling. The endotherm and the exotherm are reversible and readily reproducible, implicating a melting and re-crystallization process.

Figure 4:
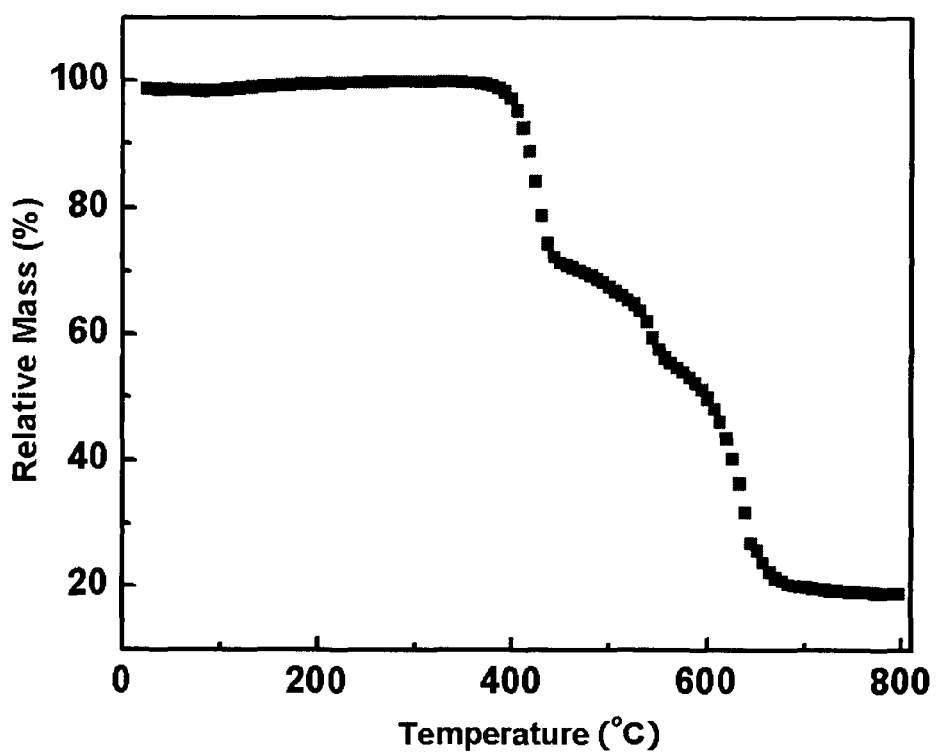
FIG. 4 provides a thermogravimetric analysis (TGA) of a compound of the present teachings.

Thermogravimetric analysis (TGA) was used to examine the thermal stability of the N-(1-hexylheptyl)perylene-3,4,9, 10-tetracarboxylic-3,4-anhydride-9,10-imide dimer 4. Using a 5% mass loss as the threshold, the onset temperature of the N-(1-hexylheptyl)perylene-3,4,9,10-tetracarboxylic-3,4-anhydride-9,10-imide dimer 4 was estimated to be around 405° C. as shown in FIG. 4.

Example 7

Device fabrication and characterization using thin films of dimers of N-(1-hexylheptyl)perylene-3,4,9, 10-tetracarboxylic-3,4-anhydride-9,10-imide 4

Prime grade n-doped silicon wafers (100) having 300 nm of thermally grown oxide (Process Specialties Inc.) were used as device substrates. These were rinsed with water, methanol, and acetone before film deposition. Trimethylsilyl functionalization of the $Si/SiO_2$ surface was carried out by exposing the silicon wafers to hexamethyldisilazane (HMDS) vapor at room temperature in a closed container under nitrogen overnight. Thin films of the N-(1-hexylheptyl)perylene-3,4,9,10-tetracarboxylic-3,4-anhydride-9,10-imide dimer 4 were drop-coated from 0.5% (w/v) THF and then annealed under nitrogen at 230-250° C. for 30 minutes. Both annealed and un-annealed devices showed very small field effect transistor (FET) activity, with carrier mobilities of $\sim 10^{-7}$ $cm^2V^{-1}s^{-1}$. X-ray diffraction data confirmed that thin films of the N-(1-hexylheptyl)perylene-3,4,9,10-tetracarboxylic-3,4-anhydride-9,10-imide dimer 4 are essentially amorphous.

The present teachings encompass embodiments in other specific forms without departing from the spirit or essential characteristics thereof. The foregoing embodiments are therefore to be considered in all respects illustrative rather than limiting on the present teachings described herein. Scope of the present teachings is thus indicated by the appended claims rather than by the foregoing description, and all changes that come within the meaning and range of equivalency of the claims are intended to be embraced therein.

What is claimed is:

1. A dimeric compound having the formula:

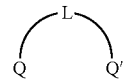

wherein:

L is a divalent $C_{1-20}$ alkyl group; and

Q and Q' have the formula:

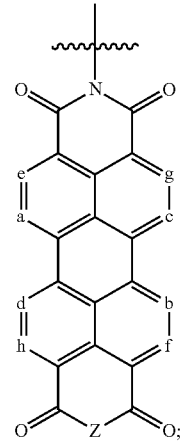

wherein:

Z is $NR^b$, wherein $R^b$ is a $C_{1-20}$ alkyl group, a $C_{1-20}$ haloalkyl group, a $C_{2-20}$ alkenyl group, a $C_{3-10}$ cycloalkyl group, or a —Y—$C_{6-14}$ aryl group optionally substituted with 1-4 groups independently selected from a halogen, a $C_{1-20}$ alkyl group, and a $C_{1-20}$ alkoxy group, wherein Y is a divalent $C_{1-20}$ alkyl group;

each of a and b is $CR^m$, wherein $R^m$ is —CN, —$OR^i$, a halogen, a $C_{1-20}$ haloalkyl group, or a 3-12 membered cycloheteroalkyl group, wherein $R^i$ is a $C_{1-20}$ alkyl group or a phenyl group optionally substituted with 1-4 $C_{1-20}$ alkyl groups; and each of c, d, e, f, g and h is CH.

2. The dimeric compound of claim 1, wherein the dimeric compound has the formula:

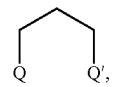

wherein Q and Q' are as defined in claim 1.

3. The dimeric compound of claim 1, wherein $R^m$ is Br, Cl, —CN, $CF_3$, N-pyrrolidine, or a 3,5-di-tert-butylphenoxy group.

4. The dimeric compound of claim 1, wherein Q and Q' have the formula:

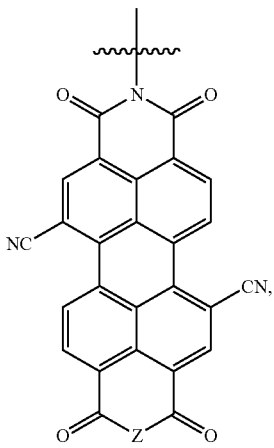

wherein Z is as defined in claim 1.

5. The dimeric compound of claim 1, wherein Z is $NR^b$ and $R^b$ is a straight chain $C_{1-20}$ alkyl group, a branched $C_{3-20}$ alkyl group, a branched $C_{4-20}$ alkenyl group, a $C_{1-20}$ fluoroalkyl group, or a $C_{3-10}$ cycloalkyl group.

6. The dimeric compound of claim 1, wherein Z is $NR^b$ and $R^b$ is —$C_8H_{17}$, —$C_{12}H_{25}$, —$CH(C_6H_{13})_2$, —$CH(C_{11}H_{23})_2$, —$CH_2C_3F_7$, or —$CH_2C_7F_{15}$.

7. The dimeric compound of claim 1, wherein Z is $NR^b$ and $R^b$ is a cyclohexyl group, a benzyl group, a 4-butyl benzyl group, a 2,3,4,5,6-pentafluorophenyl group, or a 3,4,5-tris(dodecyloxy)phenyl group.

8. A composition comprising the dimeric compound of claim 1 dissolved in an organic solvent.

9. A thin film semiconductor comprising the dimeric compound of claim 1.

10. A composite comprising a substrate and the thin film semiconductor of claim 9 deposited on the substrate.

11. An organic field effect transistor device comprising the composite of claim 10.

* * * * *